United States Patent
Schlossman et al.

(10) Patent No.: US 8,623,386 B2
(45) Date of Patent: Jan. 7, 2014

(54) NATURAL ESTER, WAX OR OIL TREATED PIGMENT, PROCESS FOR PRODUCTION THEREOF, AND COSMETIC MADE THEREWITH

(75) Inventors: David Schlossman, Short Hills, NJ (US); Yun Shao, Belle Mead, NJ (US)

(73) Assignee: Kobo Products, Inc., South Plainfield, NJ (US)

( * ) Notice: Subject to any disclaimer, the term of this patent is extended or adjusted under 35 U.S.C. 154(b) by 1006 days.

(21) Appl. No.: 12/420,498

(22) Filed: Apr. 8, 2009

(65) Prior Publication Data

US 2010/0136065 A1 Jun. 3, 2010

Related U.S. Application Data

(60) Provisional application No. 61/044,458, filed on Apr. 11, 2008.

(51) Int. Cl.
*A61K 8/02* (2006.01)
*A61K 8/19* (2006.01)

(52) U.S. Cl.
USPC ........... 424/401; 424/489; 424/490; 424/496; 424/725

(58) Field of Classification Search
USPC ............... 424/400, 401, 70.12, 725–757
See application file for complete search history.

(56) References Cited

U.S. PATENT DOCUMENTS

| 5,747,049 | A | * | 5/1998 | Tominaga | 424/401 |
| 2003/0161801 | A1 | * | 8/2003 | Yamasaki et al. | 424/65 |
| 2005/0265943 | A1 | * | 12/2005 | Geffroy-Hyland et al. | 424/70.12 |

FOREIGN PATENT DOCUMENTS

| JP | 07-173044 | | 7/1995 |
| JP | 2001-064117 | | 3/2001 |
| JP | 2001 64117 A | * | 3/2001 |
| JP | 2001-64117 A | * | 3/2001 |
| JP | 2002-363032 | | 12/2002 |

* cited by examiner

*Primary Examiner* — Michael G Hartley
*Assistant Examiner* — Micah-Paul Young
(74) *Attorney, Agent, or Firm* — Handal & Morofsky, LLC

(57) ABSTRACT

The present invention provides compositions for natural cosmetic products and, more particularly, to natural ester, wax or oil treated pigments, the products of such treated pigments and cosmetic products incorporating pigments treated with natural ingredients.

52 Claims, No Drawings

NATURAL ESTER, WAX OR OIL TREATED PIGMENT, PROCESS FOR PRODUCTION THEREOF, AND COSMETIC MADE THEREWITH

CROSS REFERENCE TO PROVISIONAL APPLICATION

The present application claims priority to U.S. Provisional Application No. 61/044,458, filed Apr. 11, 2008, which is incorporated by reference herein in its entirety.

TECHNICAL FIELD

The present invention relates to compositions for natural cosmetic products and more particularly to natural ester, wax or oil treated pigments, the products of such treated pigments and cosmetic products incorporating pigments treated with natural ingredients.

BACKGROUND OF THE INVENTION

Minerals such as talc, mica and sericite, metal oxides such as titanium dioxide, zinc oxide and iron oxides, thermoplastic powders, organic pigments such as starch and cellulose, and other inorganic pigments are widely used in cosmetic products. Although they can be used without treatment, their performance can be significantly improved through surface treatment. Special properties such as water-proofness, low oil absorption, higher solids loading, softness, enhanced dispersibility, and resistance to low pH can be enhanced through surface treatment.

Most common surface modifying agents, such as methicone, silane, dimethicone, titanate, magnesium myristate and perfluoroalcohol phosphate are all synthetic compounds and may involve undesirable complications.

SUMMARY OF THE INVENTION

In accordance with the present invention, plant derived esters and wax such as jojoba ester and jojoba wax in particular, are used to surface treat pigments and fillers. The treated pigments may be hydrophobic and have a nice skin feel and good adhesion. It is envisioned that the treated pigments in accordance with the present invention may be used in a wide range of cosmetic compositions.

In an aspect of the present invention, there is provided a cosmetic composition comprising a pigment treated with a natural surface modifying agent.

In another aspect of the present invention, there is provided a cosmetic composition comprising at least one hydrophobic natural surface modified pigment selected from titanium dioxide, yellow iron oxide, red iron oxide, black iron oxide, mica and silica, the pigment being incorporated into a cosmetic product such as lipstick, loose or pressed powder, foundation, blush and sunscreen.

In a further aspect of the present invention, there is provided a process for making a natural surface treated pigment, comprising providing a pigment; blending the pigment with a natural surface modifying agent to produce a blend; heating the blend to approximately 100 degrees C. to 110 degrees C.; and allowing the blend to cool to approximately 18 degrees C. The material may then be milled.

Natural products are believed to be more compatible with the human body and more environmentally friendly. The cosmetic products contemplated by the present invention include natural products with a smooth feel and good adhesion. It is contemplated that a variety of products may incorporate the formulation and processes provided herein. For example, emulsions such as makeup, foundation and mascara; anhydrous hot pours such as lipsticks and blush; and powders such as pressed and loose powders may be made.

In an embodiment of the present invention, there is provided a cosmetic composition comprising a pigment treated with a natural surface modifying agent. Suitable natural surface modifying agents according to the present invention include, without limitation, jojoba ester, hydrogenated jojoba oil and mixtures thereof.

Suitable pigments according to the present invention include, without limitation, minerals such as talc, mica and sericite; metal oxides such as titanium dioxide, zinc oxide and iron oxides; thermal plastic powders; and organic pigments such as starch and cellulose.

In another embodiment of the present invention, there is provided a cosmetic composition comprising at least one hydrophobic natural surface modified pigment selected from the group comprising titanium dioxide, yellow iron oxide, red iron oxide, black iron oxide, mica and silica, the pigment being incorporated into a cosmetic product selected from lipstick, loose or pressed powder, foundation, blush and sunscreen.

In an exemplary embodiment, the cosmetic composition is an oil in water liquid make-up having between about 0.5 wt. % to about 15 wt. %, preferably about 1 wt. % to about 7 wt. % and more preferably about 4.5 wt. % of a hydrophobic natural surface modified pigment selected from the group comprising titanium dioxide, yellow iron oxide and red iron oxide.

In another exemplary embodiment, the cosmetic composition is a hot pour creating a liquid compact foundation having between about 15% to about 75%, preferably about 25% to about 50% and more preferably about 40% of a natural surface modified pigment selected from the group comprising titanium dioxide, red iron oxide, yellow iron oxide, black yellow oxide, mica and silica.

In another exemplary embodiment, the cosmetic composition is a lipstick having between about 0.5% and about 20%, preferably about 2% to about 10% and more preferably about 6% of a natural surface modified pigment selected from the group comprising D&C Red No. 6 Barium Lake, D&C Red No. 7 Calcium Lake and iron oxides.

In another exemplary embodiment, the cosmetic composition is a pressed powder having between about 30% to about 85%, preferably between about 50% to about 80% and more preferably about 72% of a natural surface modified pigment selected from the group comprising sericite, yellow iron oxide, red iron oxide and black iron oxide.

In another exemplary embodiment, the cosmetic composition is an emollient loose powder having between about 0.1% to about 10%, preferably between about 0.5% to about 2% and more preferably about 0.78% of a natural surface modified pigment selected from the group comprising yellow iron oxide, red iron oxide and black iron oxide.

In a further embodiment of the present invention, there is provided a process for making a natural surface treated pigment comprising providing a pigment; blending the pigment with a natural surface modifying agent to produce a blend; heating the blend to between about 80 degrees C. to about 150 degrees C., preferably between about 100 degrees C. to about 110 degrees C.; and allowing the blend to cool to approximately 18 degrees C.

A variety of pigments may be used to make casted pigments in accordance with the present invention. For example, minerals such as talc, mica and sericite; metal oxides such as titanium dioxide, zinc oxide and iron oxides; thermoplastic powders; organic pigments such as starch and cellulose; and other inorganic pigments may be used. Materials having a large range of sizes, for example from about 5 nm to 300 nm or larger, as well as various shapes, for example, without limitation, spherical and acicular, may be treated. For example, materials that may be advantageously treated in accordance with the present invention include microparticles of the metal oxide titanium dioxide ($TiO_2$) (micro $TiO_2$) having a primary particle size of less than about 200 nm and a pigmentary grade size (i.e., larger particle size) of greater than about 200 nm, with an alumina coating such as that sold by ISK under the trade name TTO-S-3. TTO-S-3 has a primary particle size of about 15 nm and has an acicular shape. Tipaque PF-671 is an example of a pigmentary grade $TiO_2$ having an alumina and silica coating and a particle size of about 210 nm that may be treated in accordance with the present invention.

Another example of a material that may be treated in accordance with the present invention include microparticles of zinc oxide (ZnO) having a primary particle size less than about 200 nm (micro ZnO) and a pigmentary grade size of greater than about 200 nm. such as MZ-500, provided by Tayca, is a micro ZnO with a primary particle size of about 20 nm. Other examples of materials that may be used in accordance with the present invention include, without limitation, iron oxides such as those provided by Sun Chemical under the trade names C33-5198 Cosmetic Black, C33-128 Cosmetic Russet and C33-8073 Cosmetic Yellow.

Yet another material that may be treated in accordance with the invention is a macroparticle composite of smaller particles (e.g. sunscreen particles) in a binder matrix and/or a macroparticle defining voids holding smaller particles (for example, smaller sunscreen particles).

In accordance with the present invention, a natural coating is used in connection with a pigment to provide natural products with superior feel and other desirable properties. The coating may be jojoba esters, which is a complex mixture of esters produced by the transesterification/interesterification of Simmondsia Chinensis (Jojoba) oil (q.v.), hydrogenated Jojoba oil (q.v.), or a mixture of the two. In a preferred embodiment, Floraester 70 provided by Floratec is used. However, any grade of Jojoba ester may be used in accordance with the present invention.

Further, Jojoba wax, i.e., hydrogenated Jojoba oil, may be used. Jojoba wax is the end product of the controlled hydrogenation of Simmondsia Chinensis (Jojoba) Oil (q.v.).

In accordance with the present invention, it is contemplated that other natural materials may be substituted for jojoba ester. Suitable materials for use in accordance with the methods of the invention, in addition to jojoba ester, jojoba wax (that is hydrogenated jojoba oil) and jojoba oil include, without limitation, whale oil, soya wax and candelilla. Jojoba and jojoba esters, in particular, are preferred because they both are very resistant to oxidation, more so than castor oil, coconut oil, macadamia nut oil and even many fractions of mineral oil. The similarity of jojoba esters to human sebum makes jojoba-based hydrophobizing coatings particularly preferred.

It is also noted that in accordance with the invention, jojoba esters produce an unexpected array of properties in pigments which are treated with them. More particularly, titanium dioxide treated with jojoba ester gives the product a feel which is as dry as untreated pigment, but which is very smooth and on a par with the smoothness of the pigment treated with hydrogenated lecithin and stearic acid.

Jojoba ester treated sericite also scores very high on the smoothness scale, comparable to hydrogenated lecithin treated pigment and substantially more smooth than the pigment treated with lauroyl lysine or lecithin.

Pigments treated with jojoba ester are almost completely odorless, as compared to other treatments such as carnauba wax which have relatively strong odors. Likewise, when subjected to high temperatures, such as 90° C., for a relatively long time, such as six hours, pigments, such as titanium dioxide and seracite exhibit virtually no odor change, whereas pigments treated with such materials as carnauba and lauroyl lysine exhibit odor increases in the range of about 30 to 90%. Thus, pigments treated with these other materials have odor levels dozens of times greater than pigments treated in accordance with the invention, both before and after exposure to high levels of heat.

Moreover, despite the relative dryness of jojoba treated pigments, the treatment is very effective in giving mechanical stability to compacted powders, as compared to untreated pigment compacts which tend to break apart with mechanical shock and/or agitation.

The present invention is additionally described by way of the following illustrative, non-limiting examples that provide a better understanding of the present invention and of its many advantages.

EXAMPLES

Production of Coated Powders

Example 1

Hydrophobically Coating Micro $TiO_2$ 93 g of alumina treated 15 nm titanium dioxide sold under catalog number TTO-S-3 by ISK, as described above, was blended with 7 g of Jojoba ester (Floraester 70). The blend was heated to approximately 100° C.-110° C. The blend was held at a temperature of 100° C. for approximately 1 hour. The blend was then allowed to cool to room temperature, which was approximately 18° C. The powder was milled using a blender.

Example 2

Hydrophobically Coating Red Iron Oxide Pigment 97 g of red iron oxide sold under the trade name C33-128 Cosmetic Russet, as provided by Sun Chemical, was blended with 3 g of jojoba ester under the trade name Floraester 70 as provided by Floratec. The blend was heated to about 100° C.-110° C. The blend was held at a temperature of 100° C. for approximately 1 hour. The blend was then allowed to cool to room temperature, which was approximately 18° C. The powder was milled using a blender.

Example 3

Hydrophobically Coating a Pearlescent Pigment 98 g of a pearlescent pigment, such as that sold under trade name KTZ™ Interval Red as provided by Kobo Products, Inc., was blended with 2 g of Jojoba ester under the trade name Floraester 70. The blend was heated to 100° C.-110° C. The blend was held at a temperature of 100° C. for approximately 1 hour. The blend was then allowed to cool to room temperature, which was approximately 18° C. The powder was milled using a blending process with a blender.

Example 4

Hydrophobically Coating of a Microsphere 95 g of silica beads under trade name MSS-500W as provided by Kobo was blended with 5 g of Jojoba ester under trade name Floraester 70. The blend was heated to 100-110° C. The blend was held at a temperature of 100° C. for approximately 1 hour. The blend was then cooled to room temperature, which was approximately 18° C. The powder was then pulverized using a large Cuisinart food processor equipped with its S-shaped chopping blade.

Test Results

Hydrophobicity

To test hydrophobicity, approximately 0.5 g-1 g of both the uncoated powder pigments and the coated powder pigments made from the above processes according to each of the Examples 1-4 were tested. The powder pigment tested, in each case, was gently spooned onto the surface of water contained in a 4 oz. jar. The jar contained 50 mL of water.

The uncoated powders immediately sank upon addition to the jar of water. The coated powers made according to Examples 1-4 floated on the water for more than an hour. Thus, the coated powders showed hydrophobic qualities.

Skin Feel

To test skin feel, a small portion of each of the uncoated pigment powders and coated powders made in accordance with Examples 1-4 were tested. The pigment powders were placed onto and rubbed against the surface of the forearm using an index finger.

Uncoated $TiO_2$, ZnO and iron oxides with particles sizes of at least 10 nm, had an abrasive and unpleasant feel. The coated $TiO_2$, ZnO and iron oxides coated with Floraester 70 and/or Jojoba and prepared in accordance with Examples 1 and 2 provided a smooth and soft skin feel. Additionally, uncoated mica talc had a smooth feel. Talc and mica coated with Floraester 70 and Jojoba and prepared according to Example 3 also provided a smooth feel that was soft and creamy.

It is contemplated by the present invention that the treated pigments may be used in a wide variety of applications including emulsions such as makeup, foundation, mascara and sunscreens; anhydrous hot pours such as lipsticks and blush; and powders such as pressed and loose powders. Some possible applications are described below in the next set of Examples. The formulations shown are based on the total weight percentage of the formulation.

Example 5

Oil in Water Liquid Makeup

TABLE 1

| Oil in Water Liquid Makeup Ingredients | % |
|---|---|
| Part A | |
| (Oil Phase) | |
| Lanolin Alcohol and Mineral Oil | 11.50 |
| Cetyl Esters | 3.20 |
| Stearic Acid | 3.50 |
| Glyceryl Monostearate | 1.80 |
| Talc | 2.00 |
| Titanium dioxide (produced in Example 1) | 4.00 |
| Yellow iron oxide (alumina coated and processed as in Example 2) | 1.00 |
| Red iron oxide (w/alumina coated and processed as in Example 2) | 0.40 |
| Black iron oxide (w/alumina coated and processed as in Example 2) | 0.15 |
| Part B | |
| (Water Phase) | |
| Propylene glycol | 12.00 |
| Triethanolamine | 1.00 |
| PE 20 Sorbitan Monolaurate | 0.65 |
| Magnesium Aluminum Silicate | 1.00 |
| Carboxymethyl Cellulose | 0.30 |
| Deionized Water | 57.20 |
| Preservatives and Fragrance | 0.30 |

A formulation for liquid make-up is shown in Table 1. The ingredients in Part A were combined in the following order, lanolin alcohol and mineral oil, cetyl esters, stearic acid, glyceryl monostearate, talc, titanium dioxide in accordance with Example 1, yellow iron oxide in accordance with Example 2, red iron oxide in accordance with Example 2, and black iron oxide in accordance with Example 2. Each ingredient in Part A was added one at a time, mixing each component in until homogenous and then the next ingredient was added. The formulation in Part A was heated to 60° C.

In a separate vessel, the ingredients of Part B were slowly combined by being added in the following order: propylene glycol, triethanolamine, PE 20 sorbitan monolaurate, magnesium aluminum silicate, carboxymethyl cellulose, deionized water and preservatives and fragrance.

Part A was then slowly added to Part B. The Parts were mixed together using a blending process in a conventional blender. The mixture was then poured into containers.

Example 6

Liquid Compact Foundation Hot Pour

TABLE 2

| Liquid compact foundation (Hot pour) | % |
|---|---|
| Part A | |
| Titanium dioxide (w/hydrophobic performed as in Example 1) | 26.76 |
| Red iron oxide (w/hydrophobic performed as in Example 2) | 0.54 |
| Yellow iron oxide (w/hydrophobic performed as in Example 2) | 0.54 |
| Black iron oxide (w/hydrophobic performed as in Example 2) | 0.16 |
| Mica (w/hydrophobic performed as in Example 3) | 10.00 |
| Silica (spherical) (w/hydrophobic performed as in Example 4) | 2.00 |
| Part B | |
| Squalane | 10.00 |
| Dimethicone (5 cst) | 17.00 |
| Octyl hydroxystearate | 7.00 |
| Polyglyceryl-3 diisostearate | 3.00 |
| Microcrystalline wax | 7.00 |
| Octyl palmitate | 7.00 |
| Carnauba wax | 1.00 |

TABLE 2-continued

| Liquid compact foundation (Hot pour) | |
|---|---|
| | % |
| Part C | |
| Nylon-12 (12 micron spherical beads sold by Kobo Products, Inc. under catalog number SP-10.) | 8.00 |

Part A: titanium dioxide in accordance with Example 1, red iron oxide in accordance with Example 2, yellow iron oxide in accordance with Example 2, black iron oxide in accordance with Example 2, and mica in accordance with Example 3 were micronized using a mixing process until the color was fully developed. Part B: squalane, dimethicone (5 cst), octyl hydroxystearate, polyglyveryl-3 diisostearate, microcrystalline wax, octyl palmitate and carnauba wax were heated to 195° F.-200° F. while simultaneously stirring. Part B was continuously stirred for 30 minutes.

Part A was added to Part B and mixed until homogeneous. The mixture was allowed to cool to 180° F. Part C: nylon-12 was added to the mixture of Part A and Part B and mixed until homogeneous. The mixture of Part A, Part B and Part C was poured into pans at 165° F.-170° F.

Example 7

Lipstick

TABLE 3

| Lipstick | |
|---|---|
| Ingredient | % |
| Candelilla Wax | 6.00 |
| Carnauba Wax | 3.00 |
| Ozokerite | 4.00 |
| Paraffin Wax | 2.00 |
| Yellow Beeswax | 6.00 |
| Lanolin Alcohol | 6.00 |
| Oleyl Alcohol | 10.00 |
| BHA | 0.20 |
| Castor Oil | 43.25 |
| D&C Red No. 6 Barium Lake (w/coating in accordance with Example 4) | 2.50 |
| D&C Red No. 7 Calcium Lake (w/ coating in accordance with Example 4) | 2.50 |
| Iron Oxides (w/coating in accordance with Example 2) | 1.00 |
| FD&C Blue No. 1 | 0.80 |
| Perfume | 0.75 |
| Titanium Dioxide (and) Mica (w/coating) | 10.00 |

The castor oil was placed in a blender and heated to 80° C. using a steam pan. The treated pigments and the dyes including D&C red No. 6 barium lake with a coating prepared in accordance with Example 4, D&C red No. 7 calcium lake prepared in accordance with Example 4, iron oxides prepared in accordance with Example 2, and FD&C Blue No 1, were added to the castor oil using a Lightnin' mixer under high speed for 30-60 minutes.

The candelilla wax, carnauba wax, beeswax, ozokerite paraffin wax, oleyl alcohol and lanolin alcohol were preheated and melted together at 80-85° C. using a steam pan. These melted components were then added to the castor oil, pigment and dye mixture. Mixing was continuous throughout the addition of each ingredient.

The perfume was added and mixing was continued until the mixture was homogeneous. The titanium dioxide and mica were then added and mixing continued until the product was uniform.

The lipstick was then formed in a manner consistent with that known to those skilled in the art.

Example 8

Pressed Powder

TABLE 4

| Pressed Powder | |
|---|---|
| | % |
| Part A | |
| Sericite (with hydrophobic coating as in Example 4) | 70 |
| Yellow iron oxide (with hydrophobic coating as in Example 2) | 0.88 |
| Red iron oxide (with hydrophobic coating as in Example 2) | 0.76 |
| Black iron oxide (with hydrophobic coating as in Example 2) | 0.36 |
| Part B | |
| Squalane | 1.8 |
| Pentaerythritol tetraoctanoate | 1.2 |
| Dimethicone and trimethylsiloxysikiacate | 5 |
| Part C | |
| Nylon-12 (12 micron spherical beads sold by Kobo Products, Inc. under catalog number SP-10.) | 20 |

Part A: sericite with a coating of jojoba ester prepared in accordance with Example 4, yellow iron oxide prepared in accordance with Example 2, red iron oxide prepared in accordance with Example 2, and black iron oxide prepared in accordance with Example 2 were mixed together in the order listed and passed through a pulverizer until the color was fully developed.

Part B, made of squalane, pentaerythritol tetraoctanoate, dimethicone and trimethylsiloxysilicate, was pre-warmed to 65°-70° C. Part B was then sprayed onto Part A. Parts A and B were then mixed well with a blending process using a conventional blender. Part B was then passed through a pulverizer until the oil was completely dispersed. Part C, nylon-12, was added to Part B and blended well. If necessary, the mixture was passed through a pulverizer to fully develop the color. It was important not to overheat Part B. The mixture was then passed through a #20 mesh screen at 1000 psi.

The product was then pressed in a conventional manner.

Example 9

Emollient Loose Powder

TABLE 5

| Emollient Loose Powder | |
|---|---|
| | % |
| Part A | |
| Mica | 59.22 |
| Yellow iron oxide (with hydrophobically applied coating as in Example 2) | 0.24 |

TABLE 5-continued

Emollient Loose Powder

| | % |
|---|---|
| Red iron oxide (with hydrophobically applied coating as in Example 2) | 0.24 |
| Black iron oxide (with hydrophobically applied coating as in Example 2) | 0.30 |
| Part B | |
| Squalane | 6.90 |
| Pentaerythritol tetraoctanoate | 4.50 |
| Dimethicone and trimethylsiloxysilicate | 10.86 |
| Silica (Spherical) | 10.00 |

Mica, yellow iron oxide and black iron oxide which make up Part A were added to a Waring Blender under a fume hood. Part A was mixed for 2-3 minutes at high speed. Part 2, comprising the squalane, pentaerythritol tetraoctanoate, dimethicone and trimethylsiloxysikiacate and silica (spherical), were pre-blended in a Waring Blender. Part B was added to Part A and mixed. The mixture was then passed through a pulverizer until the oil was dispersed.

While the invention has been particularly shown and described with reference to preferred embodiments thereof, it will be understood by those skilled in the art that various alterations in form and detail may be made therein without departing from the spirit and scope of the invention, as defined by the appended claims.

What is claimed is:

1. Treated pigment for cosmetic compositions and sunscreens, said pigment being directly coated with an agent, said agent comprising a jojoba ester, wherein the coated pigment is hydrophobic.

2. The treated pigment of claim 1, wherein the pigment consists of one or more pigments selected from the group consisting of minerals such as talc, mica and sericite; metal oxides such as titanium dioxide, zinc oxide and iron oxides; thermal plastic powders; organic pigments such as starch and cellulose, organic lakes, combinations of any of the foregoing, and composites of one or more of the foregoing.

3. The treated pigment of claim 2, wherein the pigment comprises metal oxides, and said metal oxides are selected from the group consisting of sunscreen grades of titanium dioxide and zinc oxide, said metal oxide having a mean particle size between 10 nm and 200 nm.

4. The treated pigment of claim 2, wherein the pigment comprises metal oxides and said metal oxides are pigmentary grades of metal oxide.

5. The treated pigment of claim 2, wherein the pigment comprises a pearlescent pigment having a mean particle size of 5-200 micron.

6. The treated pigment of claim 3, wherein the pigment comprises zinc oxide with a mean primary particle size of roughly about 15 nm to 300 nm.

7. The treated pigment of claim 3, wherein the pigment comprises titanium dioxide and has a mean primary particle size of roughly about 15 nm.

8. The treated pigment of claim 2, wherein the pigment comprises silica beads with a mean particle size of 2-40 microns.

9. A cosmetic composition or sunscreen product comprised of the treated pigment of claim 1 formulated into said cosmetic composition or sunscreen product, said cosmetic composition or sunscreen product selected from the group consisting of lipstick, loose or pressed powder, foundation, cream, lotion or blush.

10. A cosmetic composition or sunscreen product comprised of the treated pigments of claim 2 formulated into a cosmetic composition or sunscreen product selected from the group consisting of lipstick, loose or pressed powder, foundation, and blush.

11. A cosmetic composition or sunscreen comprising at least one pigment selected from the group consisting of titanium dioxide, yellow iron oxide, red iron oxide, black iron oxide, mica and silica, wherein the pigment is directly coated with an agent comprising a jojoba ester, such that the pigment is rendered hydrophobic, the pigment being incorporated into a cosmetic composition or sunscreen selected from the group consisting of lipstick, loose or pressed powder, foundation, and blush.

12. The cosmetic composition of claim 11, wherein the cosmetic composition is an oil in water liquid make-up having between about 0.5 wt. % to about 15 wt. % of the hydrophobic pigment selected from the group consisting of titanium dioxide, yellow iron oxide red iron oxide, and black iron oxide.

13. The composition of claim 12, wherein the oil in water liquid make-up has between about 1 wt. % to about 7 wt. % of the hydrophobic pigment.

14. The composition of claim 13, wherein the oil in water liquid make-up has about 4.5 wt. % of the hydrophobic pigment.

15. The cosmetic composition of claim 11, wherein the cosmetic composition is a hot pour creating a liquid compact foundation having between about 15% to about 75% of the hydrophobic pigment wherein the untreated pigment is selected from the group consisting of titanium dioxide, red iron oxide, yellow iron oxide, black yellow oxide, mica and silica beads.

16. The cosmetic composition of claim 15, wherein the liquid compact foundation comprises between about 25% to about 50% of the hydrophobic pigment.

17. The composition of claim 16, wherein the liquid compact foundation comprises about 40% of the hydrophobic pigment.

18. The cosmetic composition of claim 11, wherein the cosmetic composition is a lipstick having between about 0.5% and about 20% of the hydrophobic pigment, wherein the uncoated pigment is an organic lake selected from the group consisting of D&C Red No. 6 Barium Lake, D&C Red No.7 Calcium Lake and iron oxides.

19. The composition of claim 18, wherein the lipstick comprises between about 2% to about 10% of the hydrophobic pigment.

20. The cosmetic composition of claim 11, wherein the cosmetic composition is a pressed powder having between about 30% to about 85% of the hydrophobic pigment, wherein the untreated pigment is selected from the group consisting of sericite, titanium dioxide, yellow iron oxide, red iron oxide and black iron oxide.

21. The cosmetic composition of claim 20, wherein the pressed powder has between about 50% to about 80% of the hydrophobic pigment.

22. The cosmetic composition of claim 21, wherein the pressed powder has roughly about 72% of the hydrophobic pigment.

23. The cosmetic composition of claim 11, wherein the cosmetic composition is an emollient loose powder having between about 0.1% to about 10% of the hydrophobic pigment wherein the uncoated pigment is selected from the group consisting of yellow iron oxide, red iron oxide and black iron oxide.

24. The cosmetic composition of claim 23, wherein the emollient loose powder has between about 0.5% to about 2% of the hydrophobic pigment.

25. The cosmetic composition of claim 24, wherein the emollient loose powder has about 0.78% of the hydrophobic pigment.

26. A treated pigment according to claim 1, wherein the agent comprises a mixture of esters produced by the transesterification or interesterification of Simmondsia Chinensis.

27. A treated pigment according to claim 1 wherein the agent comprises Floraester 70 or substantially the equivalent.

28. A treated pigment according to claim 1 wherein the iodine value of the agent is less than 2 g/100g.

29. A treated pigment according to claim 1 wherein the melting point of the agent is roughly about 66-70 degrees C.

30. The treated pigment of claim 6, wherein the agent consists essentially of a jojoba ester.

31. The treated pigment of claim 7, wherein the agent consists essentially of a jojoba ester.

32. A composition comprising a treated pigment wherein the mean particle size of the pigment lies substantially within the range of 5 nm to 200 microns, said pigment being directly coated with an agent to form a coated pigment, said agent comprising a jojoba ester, said jojoba ester being present in a quantity sufficient to render the coated pigment hydrophobic.

33. A composition according to claim 32 wherein the pigment is incorporated into a cosmetic composition selected from the group consisting of lipstick, loose or pressed powder, foundation, or blush, or a sunscreen.

34. A treated pigment according to claim 32 wherein the melting point of the agent is roughly about 66-70 degrees C.

35. The treated pigment of claim 32, wherein the pigment is a metal oxide suitable for a sunscreen selected from the group consisting of titanium dioxide and zinc oxide, and wherein the metal oxide particles have primary particle sizes which lie substantially within a range of less than about 300 nm.

36. The treated pigment of claim 32, wherein the metal oxide is a pigmentary grade pigment selected from the group consisting of titanium dioxide and zinc oxide.

37. A composition comprising a treated pigment, wherein the mean particle size of the pigment lies substantially within the range of 10 nm to 200 microns, said pigment being directly coated with an agent to form a coated pigment, said agent comprising a jojoba ester, said jojoba ester being present in a quantity sufficient to render the coated pigment hydrophobic.

38. A treated pigment as in claim 1, wherein the pigment is treated by directly coating the pigment by a process comprising:
providing a plurality of untreated pigment particles;
blending the untreated pigment particles with an agent comprising jojoba esters to produce a blend;
heating the blend to a temperature between about 80 degrees C. and 150 degrees C.;
allowing the blend to cool;
milling the blend to produce a resultant powder.

39. The treated pigment according to claim 38 wherein the average particle size of the pigment particles before the blending of the pigment particles with said jojoba esters is in the range of 10 nm to 200 microns.

40. The treated pigment according to claim 39 wherein the untreated pigment comprises zinc oxide.

41. The treated pigment according to claim 39 wherein the untreated pigment comprises titanium dioxide.

42. The treated pigment according to claim 38 wherein the average particle size range of the uncoated pigment is 5 nm-300 nm.

43. The treated pigment according to claim 38 wherein the iodine value is less than 2 g/100g.

44. The treated pigment according to claim 38 wherein the melting point of the agent is roughly about 66-70 degrees C.

45. The treated pigment according to claim 38 wherein the pigment is selected from the group consisting of minerals such as talc, mica and sericite; metal oxides such as titanium dioxide, zinc oxide and iron oxides; thermal plastic powders; organic pigments such as starch and cellulose, organic lakes, combinations of any of the foregoing, and composites of one or more of the foregoing.

46. The treated pigment according to claim 38 wherein the weight of the jojoba esters used to treat the untreated pigment particles is in the range of 2-8% of the weight of untreated pigment.

47. The treated pigment according to claim 38 wherein the weight of the jojoba esters used to treat the untreated pigment particles is about 2% of the weight of untreated pigment particles, or of a weight which produces results substantially the equivalent of the results of the treatment of said untreated pigment particles with said weight of jojoba esters.

48. The treated pigment according to claim 38 wherein the weight of the jojoba esters used to treat the untreated pigment particles is about 8% of the weight of untreated pigment particles, or of a weight which produces results substantially the equivalent of the results of the treatment of said untreated pigment particles with said weight of jojoba esters.

49. The treated pigment according to claim 46 wherein the untreated pigment comprises titanium dioxide, said titanium dioxide having a primary particle size of about 15 nm.

50. The treated pigment according to claim 46 wherein the untreated pigment particles comprise zinc oxide, said zinc oxide having a primary particle size in the range of about 15-300 nm.

51. The treated pigment according to claim 38 formulated into a make-up product selected from the group consisting of lipstick, loose or pressed powder, foundation, blush or a sunscreen.

52. The treated pigment of claim 38, wherein the agent consists essentially of jojoba ester.

* * * * *